United States Patent [19]

Oka et al.

[11] Patent Number: 4,789,731

[45] Date of Patent: Dec. 6, 1988

[54] SEMI-SYNTHETIC PEPTIDE ANTIBIOTICS

[75] Inventors: Masahisa Oka, Yokohama; Keiichi Numata, Tokyo; Masataka Konishi, Kawasaki, all of Japan

[73] Assignee: Bristol-Myers Company, New York, N.Y.

[21] Appl. No.: 115,072

[22] Filed: Oct. 30, 1987

Related U.S. Application Data

[62] Division of Ser. No. 917,575, Oct. 10, 1986.

[51] Int. Cl.[4] ............................................. C07K 5/12
[52] U.S. Cl. ................................................... 530/317
[58] Field of Search .............................. 530/317, 321

[56]  References Cited

U.S. PATENT DOCUMENTS 4,692,510 9/1987 Konishi ............................ 540/460

Primary Examiner—Delbert R. Phillips
Assistant Examiner—Christina Chan
Attorney, Agent, or Firm—Mollie M. Yang

[57]  ABSTRACT

Semi-synthetic derivatives of the BU-2867T antibiotics are disclosed. These derivatives are active against experimental mammalian tumors, and may be prepared from enzymatic degradation product(s) of BU-2867T A.

4 Claims, No Drawings

SEMI-SYNTHETIC PEPTIDE ANTIBIOTICS

This is a divisional application of Ser. No. 917,575 filed on Oct. 10, 1986.

BACKGROUND OF THE INVENTION

1. Field of Invention

The present invention relates to novel semi-synthetic peptide antibiotics, to processes of their production, and to their use as agents for inhibiting mammalian neoplasms.

2. Description of the Prior Art

Disclosed in our co-pending application U.S. Ser. No. 855,649, filed Apr. 25, 1986, now U.S. Pat. No. 4,692,510, are peptide antibiotics BU-2867T A, B, and C having the formula I wherein E represents the trans configuration of the double bond

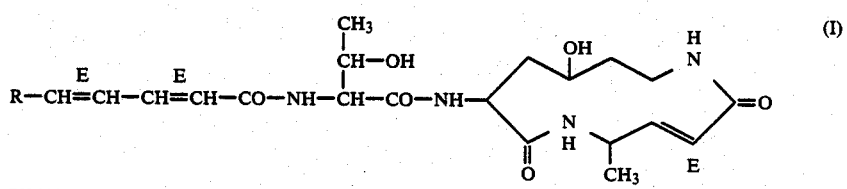

BU-2867T
A: R = $CH_3-(CH_2)_6-$
B: R = $CH_3-(CH_2)_4-CH=CH-(CH_2)_2-$
C: R = $CH_3-(CH_2)_8-$

BU-2867T, A, B, and C are produced by fermentation using the novel microorganisms *Polyangium brachysporum* strain K481-B101 (deposited with the ATCC and assigned the culture No. 53,080); they are useful as antitumor and antifungal agents.

The BU-2867T antibiotics yield useful synthetic intermediates when subjected to enzymatic cleavage. For example, when BU-2867T A was treated with the enzyme papain, a compound having the formula II (hereinafter referred to as "Compound II")

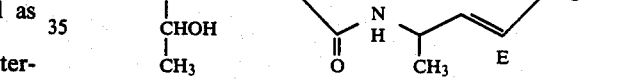

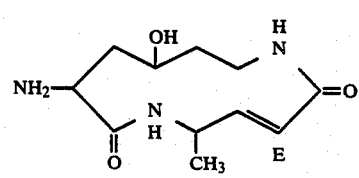

was obtained. Treatment of BU-2867T A with Pseudomonas acylase yielded a compound having the formula III (hereinafter referred to as "Compound III").

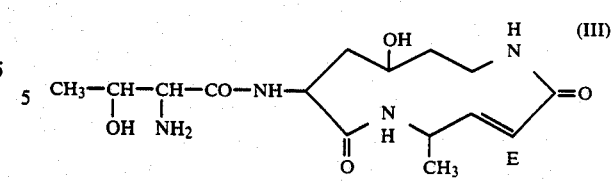

The present invention takes advantage of the synthetic utility of intermediate compounds II and III to provide novel antitunor semi-synthetic derivatives of antibiotics BU-2867T A, B, and C.

SUMMARY OF THE INVENTION

The present invention provides novel peptide antibiotics of the formula

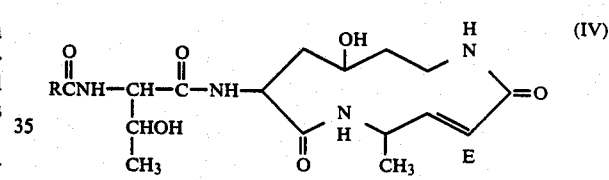

wherein the threonyl unit is L-threonyl, and wherein R is a straight chain alkyl group having 8 to 16 carbon atoms; or a group selected from the group consisting of $CH_3-(CH_2)_8-CH=CH-$, $CH_3-(CH_2)_{13}-CH(OH)-$, and $p-CH_3-(CH_2)_7-O-C_6H_4-$.

In another aspect, the present invention provides peptide antibiotics of the formula

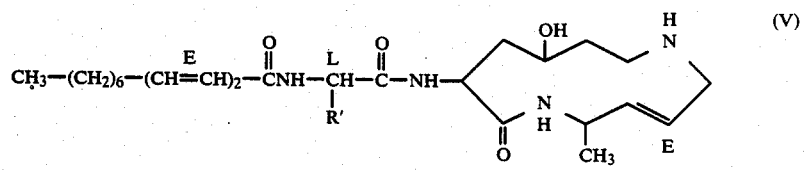

wherein R' is selected from the group consisting of ethyl, $$-(CH_2)_4NH\overset{O}{\overset{\|}{C}}-O-CH_2Ph, \text{ and } -(CH_2)_2CO_2CH_3.$$

Another aspect of the present invention provides a process for the preparation of compounds of the formula IV which comprises acylating compound III or a salt thereof, with a carboxylic acid $RCO_2H$, wherein R is as defined above, or an acylating agent corresponding thereto.

Another aspect of the present invention provides a process for the preparation of compounds of the formula IV or V which comprises acylating compound II or a salt thereof, with an acid

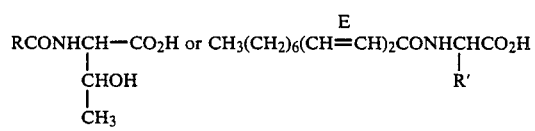

wherein R and R' are as defined above, or an acylating agent corresponding thereto, to yield IV or V respectively.

A further aspect of the present invention provides an antitumor composition comprising an effective amount of a compound of formula IV or a compound of formula V, and a pharmaceutically acceptable carrier.

Yet another aspect of the present invention provides a method for inhibiting tumors in a mammalian host which comprises administering to said tumor bearing host an effective amount of a compound of formula IV or a compound of formula V.

DETAILED DESCRIPTION OF THE INVENTION

Compounds of the present invention having the general formula IV may be prepared by either route (a) or route (b) depicted in Scheme I.

Scheme I

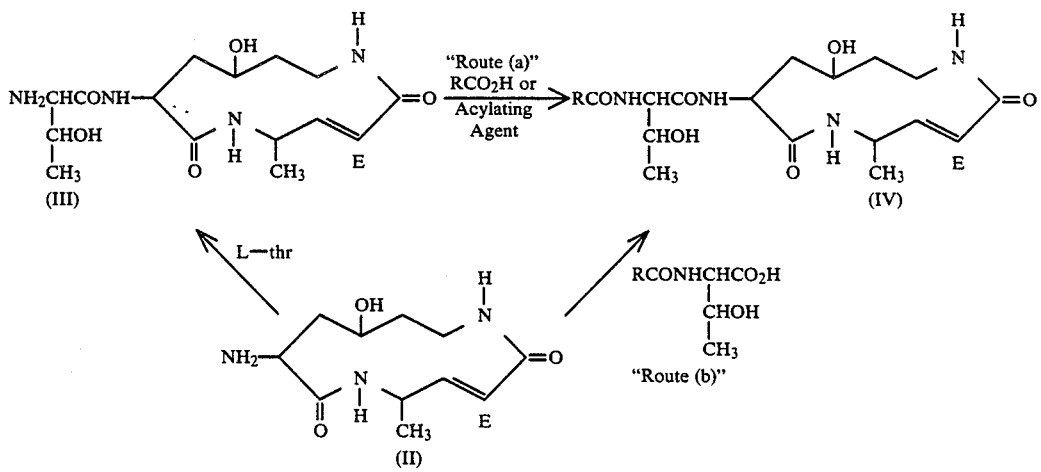

Route (a) describes the preparation of compounds of formula IV which involves acylating the amino group of compound III with an appropriate acid or an acylating agent derived therefrom. Alternatively, compounds of formula IV may be prepared by acylating the amino group of compound II with the appropriate acyl-L-threonine or a corresponding acylating agent; this latter process is outlined as route (b). Compounds II and III are enzymatic cleavage products derived from BU-2867T A, and their preparations are described in detail below in "Preparation of Starting Materials". Compound III may also be formed by condensation between L-threonine and Compound II.

Compounds of formula V may be prepared by the procedure outlined in Scheme II using compound II as starting material.

Scheme II

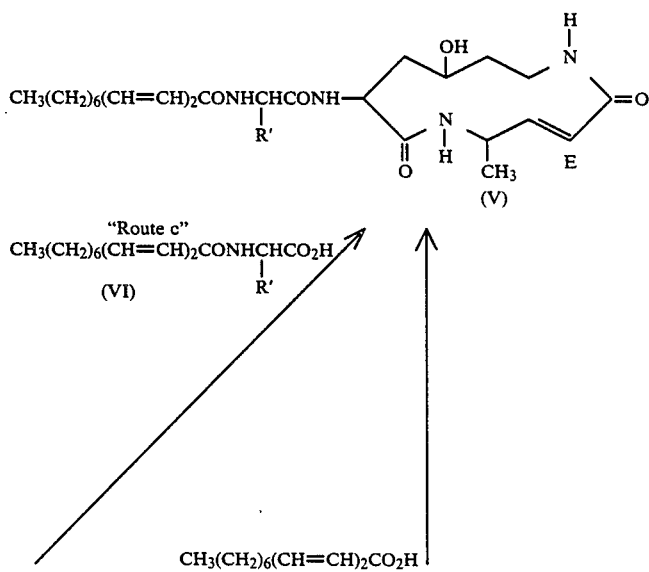

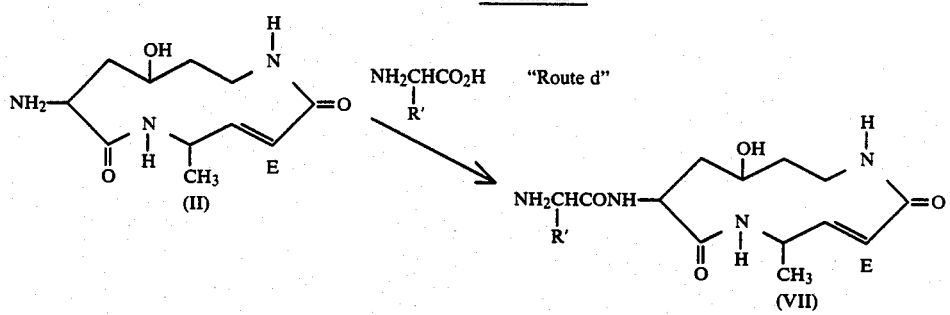

Scheme II

As shown in Scheme II route (c), compound II when acylated with a 2,4-dodecadienoylamino acid VI yields the corresponding compound V; said compound VI being formed by the condensation of 2,4-dodecadienoic acid with an appropriate α-amino acid. The order of the reaction sequence may be modified so that compound II is first coupled with an appropriate α-amino acid having the desired side chain to give compound VII which may then be further acylated with 2,4-dodecadienoic acid to produce compounds of formula V. This process is outlined as route (d).

Each of the reaction steps described in Schemes I and II involves the acylation of an amino group with a carboxylic acid or a corresponding acylating agent to form an amide bond. Acylation of amino group is a common reaction and may be accomplished by conventional methods well known to those skilled in the art. The amino compound being acylated may be employed as the free base, an acid addition salt thereof, or a reactive derivative of the amino group thereof. The acylating agent may be a symmetrical or mixed acid anhydride; an acid halide such as the acid chloride preferably used in the presence of an acid scavenger such as triethylamine; a reactive ester, e.g. with hydroxybenzotriazole; a reactive amide, e.g. with triazole; or the free acid used in conjunction with a coupling agent such as N,N'-dicyclohexylcarbodiimide.

In carrying out the reactions described above, it may be advantageous to protect certain reactive functional groups other than the reacting ones. In the case when compound II is acylated with an α-amino acid (e.g. Scheme I, Compound II+L-threonine→Compound III), the non-reacting α-amino group of the amino acid is desirably protected with an easily removable group such as t-butoxycarbonyl (t-BOC). The amino protecting group may be removed after acylation using known methods to allow the deprotected amino group to be coupled with a carboxylic acid to form a second amide linkage (e.g. Scheme I, Compound III and RCO$_2$H-→Compound IV). Other non-reacting hydroxyl, amino, and carboxyl groups may also be conventionally protected; the protective groups may be removed by known methods, if so desired, after the acylation. Techniques for protection and deprotection of reactive groups are described, for example, in J. F. W. McOmie Ed., "Protective Groups in Organic Chemistry", pp. 182 (1973), Plenum Press, N.Y.; S. Patai Ed., "The Chemistry of Functional Groups", pp 505 (1969), Interscience Publ., John Wiley and Sons, Ltd., London. Typical protection techniques are, e.g., acylation and etherification for hydroxy; e.g., acylation, enamine formation, and silyl introduction for amino; and e.g. esterification, amidation, and acid anhydride formation, for carboxy.

The acylation reactions are generally carried out in an inert solvent. Suitable solvents include, but are not limited to, methanol, ethanol, dimethylformamide, tetrahydrofuran, and the like. The reactions may be effected at temperatures ranging from about 0° to about 100° C., but preferably at room temperature.

BIOLOGICAL ACTIVITY

Antitumor activity of representative compounds of the present invention was determined using in vivo murine transplantable P388 leukemia and B16 melanoma models.

IN VIVO MODELS

P388 leukemia: female CDF$_1$ and male BDF$_1$ mice were inoculated by intraperitoneal injection of 0.8 ml diluted ascitic fluid containing 10$^6$ cells.

B16 melanoma: male BDF$_1$ mice were implanted with 0.5 ml of a 10% tumor brei intraperitoneally.

DRUG ADMINISTRATION

Test materials were dissolved in 0.9% saline containing 10% dimethyl sulfoxide and graded doses of them were administered to mice intraperitoneally 24 hrs after tumor implantation. Two dosing schedules were used for the P388 leukemia experiment: once daily on day 1 through day 3 (QD 1→3); and once daily on day 1 through day 9(QD 1→9). The QD 1→9 schedule was used for the B16 melanoma experiment.

CRITERIA FOR ANTITUMOR ACTIVITY

Antitumor activity is evaluated as the increase in median survival time (MST) of treated (T) and control (C) animals for various dosage regimens expressed as a percentage ratio (T/C %=MST of treated÷MST of control×100). For both in vivo P388 leukemia and in vivo B16 melanoma models, values for percentage ratios of 125 and above indicate significant antitumor effect.

Results of antitumor evaluation are given below in Tables 1-3.

TABLE 1

| Antitumor Effect Against P388 Leukemia | | | | |
|---|---|---|---|---|
| Compound of | MST (% T/C) dose (mg/kg/day, QD 1 → 3 ip) | | | |
| Example | 10 | 3 | 1 | .3 |
| | 155 | 145 | 130 | |
| 2 | 64 | 127 | 123 | |
| 3 | 55 | 132 | 127 | |
| 4 | | 118 | 132 | 118 |
| 5 | 132 | 132 | 118 | |

TABLE 1-continued

| Antitumor Effect Against P388 Leukemia | | | | |
|---|---|---|---|---|
| Compound of | MST (% T/C) dose (mg/kg/day, QD 1 → 3 ip) | | | |
| Example | 10 | 3 | 1 | .3 |
| 6 |  | Tox | 150 | 125 |
| 7 | Tox | 138 | 119 |  |
| 8 | 127 | 114 | 100 |  |
| 9 | Tox | 132 | 123 |  |
| 10 | 138 | 119 | 114 |  |
| BU-2867T A |  | Tox | 145 | 130 |
| C |  | 57 | 129 | 124 |

TABLE 2

| Antitumor Effect Against P388 Leukemia (QD 1 → 9 ip) | | | | | | | |
|---|---|---|---|---|---|---|---|
| Compound of | MST (% T/C) Dose (mg/kg/day, QD 1 → 9 ip) | | | | | | |
| Example | 4 | 2 | 1 | 0.5 | 0.25 | 0.13 | 0.63 |
| 1 | 173 | 159 | 150 | 145 | 132 | 127 |  |
| 2 | 155 | 145 | 127 | 123 | 123 | 109 |  |
| 3 | 159 | 150 | 150 | 132 | 132 | 118 |  |
| 6 |  |  | Tox | 155 | 150 | 140 | 120 |
| BU-2867T A |  | Tox | 190 | 155 | 150 | 130 | 110 |
| B | Tox | 180 | 170 | 145 | 130 | 125 | 130 |
| C | 65 | 205 | 170 | 155 | 160 | 130 | 115 |

TABLE 3

| Antitumor Effect Against B16 Melanoma | | | | | |
|---|---|---|---|---|---|
| Compound of | MST (% T/C) Dose (mg/kg/day, QD 1 → 9 ip) | | | | |
| Example | 4 | 2 | 1 | .5 | .25 | .13 |
| 1 | 155 | 139 | 121 | 113 | 107 |  |
| 3 | 145 | 124 | 116 | 113 | 113 |  |
| BU-2867T A |  | Tox | 116 | 113 | 100 | 97 |
| B |  | Tox | 126 | 118 | 111 | 108 |
| C | Tox | 132 | 113 | 103 | 103 | 103 |

The acute toxicity for compounds of Examples 1, 2, and 3 was determined in ddY mice by single intraperitoneal administration. The LD50 values were 27 mg/kg, 50 mg/kg, and >25 mg/kg, respectively.

It is apparent from the animal test results provided above that compounds of formula IV and V possess effective inhibitory action against mammalian tumors. Accordingly, this invention provides a method for inhibiting mammalian tumors which comprises administering an effective tumor-inhibiting dose of a compound of formula IV or V to a tumor bearing host.

Another aspect of this invention provides a pharmaceutical composition which comprises an effective tumor-inhibiting amount of a compound of formula IV or V and a pharmaceutically acceptable carrier. These compositions may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples serve to illustrate this invention and should not be construed as limiting the scope of the invention.

PREPARATION OF STARTING MATERIALS

Preparation 1

BU-2867T A, B, and C

Antibiotic Production:

The stock culture of *Polyangium brachysporum* K481-B101 (ATCC 53080) was propagated at 28° C. for 3 days on agar slant medium composed of 0.5% soluble starch, 0.5% glucose, 0.1% meat extract, 0.1% yeast extract, 0.2% NZ-case (Humko Sheffield Chemical), 0.2% NaCl, 0.1% $CaCO_3$ and 1.6% agar (pH 7.0). A well grown agar slant was used to inoculate the vegetative medium consisting of 2% corn starch, 3% soybean meal, 0.3% $MgSO_4.7H_2O$ and 1% $CaCO_3$ (pH 7.0, before sterilization). After incubation at 28° C. for 3 days on a rotary shaker (250 rpm), 5 ml of the growth was transferred into a 500-ml Erlenmeyer flask containing 100 ml of the production medium having the same composition as the vegetative medium.

The antibiotic production was monitored by the paper disc agar diffusion method using *Candida albicans* A9540 as the test organism. The fermentation was continued for 4 days at 28° C. on a rotary shaker and the antibiotic production reached a maximum of 100 mcg/ml.

The fermentation was also carried out in a stir-jar fermenter. A 500-ml portion of the seed culture obtained by flask fermentation was used to inoculate 10 liters of the production medium in a 20-liter vessel. The fermentation was carried out at 28° C. with agitation at 250 rpm and aeration at 10 liters per minute. The antibiotic production reached a maximum of 150 mcg/ml after forty hours' fermentation.

Isolation and Purification of Antibiotic:

The fermentation broth (48 L) was centrifuged with the aid of a Sharpless centrifuge. The mycelial cake was homogenized with 7 L of methanol and the mixture stirred for one hour. After removal of the insolubles by filtration, the methanol extract was evaporated to an aqueous solution which was combined with the broth filtrate and extracted with n-butanol (24 L). The extract was concentrated to 0.5 L which was poured into n-hexane (3.5 L) under stirring to precipitate the crude antibiotic (41 g). This solid was chromatographed on a column of silica gel C-200 (760 ml) eluting with ethyl acetate and an increasing amount of methanol (0–50%). The bioactivity eluted was detected by a paper disc assay using *Candida albicans* A9540 as the test organism. The active fractions were combined and evaporated to yield a pale yellow powder (13 g) of BU-2867T complex. A 200 mg-portion of this solid was chromatographed on a reverse-phase column ($C_{18}$, 100ml) using ethanol-water (3:7 to 5:5) as an eluant. The eluate was monitored by anti-fungal bioassay and by TLC (Silanized, $EtOH:H_2O=55:45$). The first active fractions were combined and evaporated under reduced pressure to afford a pure white solid of BU-2867T A (60 mg) which was crystallized from aqueous methanol to deposit colorless needles (34 mg). Evaporation of the second and third active fractions yielded BU-2867T B (1 mg) and C (11 mg), respectively. BU-2867T B was obtained as a white amorphous powder. BU-2867T C crystallized from methanol as fine colorless needles. Repetition of the above reverse-phase chromatography afforded a total of 3.9 g of BU-2867T A, 44 mg of BU-2867T B and 342 mg of BU-2867T C.

BU-2867T A: mp 259°–261° C.; $[\alpha]_D^{24°}$ (C 0.5 MeOH): −111°; EI-MS: m/z 520 (M+).

Anal calc'd for $C_{27}H_{44}N_4O_6 \cdot \frac{1}{2}H_2O$: C, 61.22; H, 8.56; N, 10.58. Found: C, 60.90; H, 8.65; N, 10.47.

BU-2867T B: mp 232°–234° C.; $[\alpha]_D^{24°}$ (C 0.5 MeOH): −92°; EI-MS: m/z 546 (M+).

Anal Calc'd for $C_{29}H_{46}N_4O_6 \cdot 3/2H_2O$: C, 60.71; H, 8.61; N, 9.77. Found: C, 60.89; H, 8.31; N, 9.23.

BU-2867T C: mp 273°–275° C.; $[\alpha]_D^{24°}$ (C 0.5 MeOH): −104°; EI-MS: m/z 548 (M+).

Anal calc'd for $C_{29}H_{48}N_4O_6$: C, 63.48; H, 8.82; N, 10.21. Found: C, 63.48; H, 8.91; N, 10.16.

PREPARATION 2

Compound II

A mixture of BU-2867T A (4 g) and papain (Sigma P-3375, 50 g) in 20 L of 10% aqueous methanol was stirred at 28° C. for 22 hours. The mixture was then acidified to pH 3.3 by acetic acid and extracted with ethyl acetate (10 L). The ethyl acetate extract yielded 2,4-dodecadienoyl-L-threonine. The acid aqueous solution was concentrated to dryness. The residue (36 g) was dissolved in 50 ml of water, adjusted to pH 9.0 and applied on a column of reverse phase silica ($C_{18}$, Merck, 1.6 L) which was developed with water. The fractions containing the title compound were pooled and concentrated in vacuo. The residue was chromatographed on Sephadex LH-20 (250 ml) with 50% aqueous methanol and then on reverse phase silica ($C_{18}$) with acidic water (pH 3.0 by dil HCl) to afford 747 mg pure II hydrochloride (yield 35%). Mp 190° C. (dec.). $[\alpha]_D^{26} -113°$ (c 0.5, $H_2O$). EI-MS: m/z 241 (M+). UV: end absorption. IR $\nu_{max}$(KBr) cm$^{-1}$: 3400, 1660, 1620, 1530, etc. $^1$H-NMR (ppm, 80 MHz, DMSO-d$_6$) δ 1.27 (3H, d), 1.4–1.8 (4H), 2.98 (2H, m), 4.52 (1H, m), 6.19 (1H, d), 6.45 (1H, d-d), 7.43 (1H, t, NH), 9.46 (1H, d, NH).

Analysis calc'd for $C_{11}H_{19}N_3O_3 \cdot HCl \cdot H_2O$: C, 44.67; H, 7.50; N, 14.21; Cl, 11.99. Found: C, 45.04; H, 7.82; N, 13.81; Cl, 12.55.

Alternatively, BU-2867T A was subjected to enzymatic degradation with ficin in 0.01M phosphate buffer (pH 7.0). The reaction mixture was acidified to pH 2.2, and extracted with n-butanol to give 2,4-dodecadienoyl-L-threonine. Subsequent extraction of the aqueous solution at pH 10.0 with n-butanol afforded the title compound.

PREPARATION 3

L-Threonyl-II (Compound III)-Method 1

Pseudomonas strain Pa-129 was fermented in 10 L of medium containing 2% soluble starch, 0.2% glucose, 3% soybean meal, 1% $CaCO_3$ and 0.3% $MgSO_4 \cdot 7H_2O$ at 37° C. for 3 days and the cells were collected by centrifugation. After being washed with saline (1 L) two times, the cells were resuspended in 0.75 L of saline. The cell suspension was mixed with a pre-autoclaved suspension (1.5 L) of sodium alginate (75 g) and CM-cellulose (75 g), and the mixture poured into 30 L of 0.1M $CaCl_2$ solution under stirring. The gel entrapping the cells was stiffened by stirring with 25% glutaldehyde solution and packed in a column (4.0×175 cm). A solution of BU-2867T A (1.5 g) in 20% aqueous methanol (30 L) was passed through the column at a flow rate of 0.4–0.8 L/hour. The pooled effluent was then passed through an Amberlite IRC-50 (70% $NH_4^+$ form, pH 6.7, 300 ml) and a HP-20 column (300 ml) successively. The IRC-50 column was washed with water and then developed with 1.5N $NH_4OH$. The ninhydrin positive fractions were pooled, concentrated and lyophilized to give a pale yellow solid (800 mg) which was charged on a column of reverse phase silica ($C_{18}$, 250 ml). The column was developed with water under medium-pressure and the ninhydrin-positive eluates were pooled and concentrated to yield a white solid of L-threonyl-II (III, 612 mg). Yield 62%. Mp 170° C., $[\alpha]_D^{27} -157°$ (C 0.5, $H_2O$). EI-MS: m/z 342 (M+). UV: end absorption. IR $\nu_{max}$ (KBr) cm$^{-1}$: 3350, 3280, 1650, 1620, 1530 etc. $^1$H-NMR (ppm, 80 MHz, DMSO-d$_6$) δ 1.05 (3H, d), 1.21 (3H, d), 1.4–2.2 (4H), 4.35 (2H, m), 4.47 (1H, m, OH), 4.62 (1H, d, OH), 6.16 (1H, d), 6.42 (1H, d-d), 7.36 (1H, t, NH), 7.97 (1H, d, NH), 8.62 (1H, d, NH).

PREPARATION 4

L-Threonyl-II (Compound III)-Method 2

To a stirred mixture of N-t-butoxy-carbonyl-L-threonine (44 mg), N,N'-dicyclohexylcarbodiimide (40 mg) and 1-hydroxy-1,2,3-benzotriazole (30 mg) in dimethylformamide (4 ml) was added II (40 mg) at room temperature. The mixture was concentrated in vacuo to a residue which was chromatographed on a column of reverse phase silica ($C_{18}$, 40 ml) with methanol and water mixture (ratios: 1:9 to 2:3). The appropriate fractions were pooled, concentrated in vacuo and lyophilized to yield N-BOC-L-threonyl II (=BOC-III). 51 mg Yield, 60%. A mixture of BOC-III (36 mg) and formic acid (1 ml) was stirred for 1 hour at room temperature. This mixture was concentrated, diluted with water (1 ml), adjusted to pH 10.0 and applied to a column of reverse phase silica ($C_{18}$, 20 ml). The column was developed with water and the eluate was monitored with ninhydrin test. Fractions containing the desired compound were combined and freeze-dried to give white solid of III. 25 mg Yield 88%.

EXAMPLE 1 n-Dodecanoyl-III

A mixture of compound III (21 mg, 0.06 mM) and dodecanoic anhydride (24 mg, 0.06 mM) in 1 ml of dimethylformamide (DMF) was stirred overnight at room temperature. The mixture was diluted with 6 ml of MeOH and 4 ml of water and the solution applied on a column of reverse phase silica gel ($C_{18}$, 40 ml). Upon elution with 70% MeOH, fractions containing the desired compound were pooled, evaporated and lyophilized to afford the title compound as a white amorphous solid (28 mg, 89%). Mp 274° C. EI-MS: m/z 524 (M+). $^1$H-NMR (ppm, 80 MHz, DMSO-d$_6$) δ: 0.86 (3H, t), 1.02 (3H, d), 6.11 (1H, d), 6.41 (1H, d-d), 7.36 (1H, t), 7.60 (2H, m), 8.55 (1H, d).

EXAMPLE 2 n-Decanoyl-III

Following the procedure described in Example 1, compound III was acylated using n-decanoic anhydride to give the title compound. Mp 244° C. $^1$H-NMR (ppm, 80 MHz, DMSO-d$_6$) at δ: 0.86 (3H, t), 1.02 (3H, d), 6.10 (1H, d), 6.40 (1H, d), 7.35 (1H, t), 7.58 (1H, d), 7.60 (1H, d), 8.56 (1H, d).

EXAMPLE 3 n-Tetradecanoyl-III

Following the procedure described in Example 1, compound III was acylated using n-tetradecanoic anhydride to give the title compound. Mp 239° C. $^1$H-NMR (ppm, 80 MHz, DMSO-d$_6$) at δ: 0.86 (3H, t), 1.00 (3H, d), 6.10 (1H, d), 6.40 (1H, d-d), 7.36 (1H, t), 7.58 (1H, d), 7.60 (1H, d), 8.56 (1H, d).

EXAMPLE 4 trans-2-Dodecenoyl-III

A mixture of trans-2-dodecenoic acid (13 mg, 0.064 mM), N,N'-dicyclohexylcarbodiimide (DCC, 10 mg, 0.064 mM) and 1-hydroxy-1,2,3-benzotriazole monohydrate (HOBT, 13 mg, 0.064 mM) in 2 ml of DMF was stirred for 2 hours at room temperature. Compound III (20 mg, 0.058 mM) was added to the solution and the mixture was stirred overnight. After dilution with 60% aqueous MeOH (5 ml), the reaction mixture was chromatographed on a reverse phase silica gel (C$_{18}$, 30 ml) with 70% MeOH elution. Fractions containing the desired compound were pooled, concentrated in vacuo, and lyophilized to give the title compound as a white solid (25 mg, 83%). Mp 232° C. $^1$H-NMR (ppm, 80 MHz, DMSO-d$_6$) at δ: 0.86 (3H, t), 1.02 (3H, d), 6.05 (1H, d), 6.10 (1H, d), 6.40 (1H, d-d), 6.50 (1H, m), 7.36 (1H, t), 7.66 (1H, d), 7.79 (1H, d), 8.55 (1H, d).

EXAMPLE 5

2-Hydroxy-hexadecanoyl-III

The title compound was obtained following the procedure described in Example 4 using an equimolar amount of 2-hydroxy-hexadecanoic acid in place of trans-2-dodecenoic acid. Mp 229° C. $^1$H-NMR (ppm, 80 MHz, DMSO-d$_6$) at δ: 0.86 (3H, t), 1.00 (3H, d), 6.11 (1H, d), 6.40 (1H, d-d), 7.35 (1H, t), 7.60 (2H, m), 8.58 (1H, d).

EXAMPLE 6 p-n-Octyloxybenzoyl-III

A mixture of p-n-octyloxybenzoic acid (25 mg, 0.1 mM), N,N'-dicyclohexylcarbodiimide (DDC, 21 mg, 0.1 mM) and 1-hydroxy-1,2,3-benzotriazole monohydrate (HOBT, 16 mg, 0.1 mM) in 3 ml of dimethylformamide was stirred for 2 hours at room temperature. To the solution was added compound III (34 mg, 0.1 mM) and the stirring was continued overnight at room temperature. The mixture was filtered, diluted with 2 ml of 50% aqueous MeOH and loaded on a column of reversed phase silica gel (C$_{18}$, 20 ml). The column was washed with 50% aqueous MeOH (250 ml), followed by elution with 80% aqueous MeOH. The fractions containing the major reaction product were pooled, evaporated and lyophilized to give a white amorphous solid of the title compound (41 mg, 71%). Mp 251° C. $^1$H-NMR (ppm, 80 MHz, DMSO-d$_6$) δ: 0.86 (3H, t), 1.05 (3H, d), 6.10 (1H, d), 6.40 (1H, d-d), 6.96 (2H, d), 7.36 (1H, t), 7.83 (2H, d), 7.96 (1H, d), 8.57 (1H, d).

EXAMPLE 7

α-(2,4-Dodecadienoylamino)-n-butyryl-II

A mixture of 2,4-dodecadienoic acid (50 mg, 0.26 mM), DCC (58 mg, 0.28 mM) and HOBT (43 mg, 0.28 mM) in tetrahydrofuran (THF, 5 ml) was stirred for one hour at room temperature. The mixture was filtered and the filtrate was added into a vigorously stirred solution of L-α-amino-n-butyric acid (52 mg, 0.5 mM) and triethylamine (0.13 ml) in 50% aqueous THF (2 ml). The reaction mixture was stirred for 4 hours, concentrated to 1 ml under reduced pressure, and the concentrate diluted with 5 ml of water. The solution was washed with ethyl acetate (EtOAc, 5 ml), acidified to pH 2.0 and extracted with EtOAc (5 ml). Evaporation of the extract gave α-(2,4-dodecadienoylamino)-n-butyric acid (64 mg 90%) as a pale yellow solid.

The acid (28 mg, 0.1 mM) was dissolved in 5 ml of DMF containing DCC (21 mg, 0.1 mM) and HOBT (15 mg, 0.1 mM) and the mixture was stirred for one hour. Compound II (24 mg, 0.1 mM) was then added to the solution and the solution was stirred overnight at room temperature. Concentration of the solution in vacuo yielded an oily residue which was loaded on a column of reverse phase silica gel (C$_{18}$, 40 ml). The column was eluted with 80% aqueous MeOH, and fractions containing the reaction product were pooled, concentrated and freeze-dried to give a white solid of the title compound (17.6 mg, 35%), Mp 254° C. EI-MS (m/z): 504 (M+). $^1$H-NMR (ppm, 80 MHz, DMSO-d$_6$) δ: 0.86 (3H, t), 0.89 (3H, t), 6.20 (5H, m), 7.00 (1H, m), 7.35 (1H, t), 7.85 (1H, d), 7.97 (1H, d), 8.54 (1H, d).

EXAMPLE 8

2,4-Dodecadienoyl-L-ω-benzyloxycarbonyl-lysyl-II

The general procedure described in Example 7 was repeated except L-α-amino-n-butyric acid was replaced by an equimolar amount of ω-benzyloxycarbonyl-L-lysine, to give the title compound in 41% yield. Mp 182° C. $^1$H-NMR (ppm 80 MHz, DMSO-d$_6$) δ: 0.86 (3H, t), 4.98 (2H, s), 6.20 (5H, m), 6.90 (1H, m), 7.14 (1H, br-s), 7.30 (6H, m), 7.97 (2H, br-d), 8.60 (1H, m).

EXAMPLE 9

2,4-Dodecadienoyl-L-ω-methyl-glutamyl-II

The general procedure described in Example 7 was repeated, except L-α-amino-n-butyric acid was replaced by an equimolar amount of ω-methyl-L-glutamic acid, to give the title compound in 44% yield. Mp 215° C. $^1$H-NMR (ppm, 80 MHz, DMSO-D$_6$) δ: 0.86 (3H, t), 3.56 (3H, s), 6.30 (5H, m), 7.00 (1H, m), 7.35 (1H, t), 8.05 (2H, m), 8.55 (1H, d).

EXAMPLE 10

Palmitoyl-L-Threonyl-II

The general procedure described in Example 7 was repeated, except L-α-amino-n-butyric acid was replaced by an equimolar amount of L-threonine, and 2,4-dodecadienoic acid replaced by an equimolar amount of palmitic acid, to give the title compound 18% yield. Mp 216° C. EI-MS (m/z): 580 (M+). $^1$H-NMR (ppm, 80 MHz, DMSO-d$_6$) δ: 0.86 (3H, t), 1.00 (3H, d). 6.10 (1H, d), 6.40 (1H, d-d), 7.35 (1H, t), 7.60 (2H, br-d), 8.56 (1H, d).

The title compound is also produced if the general procedure of Example 1 is followed with dodecanoic anhydride replaced by an equimolar amount of palmitoyl anhydride. Similarly, replacing trans-2-dodecenoic acid of Example 4 with palmitic acid results in the title compound.

EXAMPLE 11

Compounds of Examples 1 to 6 are prepared if the general procedure of Example 7 is repeated with L-α-amino-n-butyric acid replaced by an equimolar amount of L-threonine and 2,4-dodecadienoic acid by an equimolar amount of the acids listed below.

| Acid | Compound of Example |
|---|---|
| n-Dodecanoic | 1 |
| n-Decanoic | 2 |
| n-Tetradecanoic | 3 |
| trans-2-Decenoic | 4 |
| 2-Hydroxydecanoic | 5 |
| p-n-Octyloxybenzoic | 6 |

EXAMPLE 12

Compounds of Examples 7, 8, and 9 are prepared if the general procedure described in Example 4 is repeated with Compound III replaced by an equimolar amount of L-α-amino-n-butyryl-II (VIII), L-ω-benzyloxycarbonyl-lysyl-II (IX), or L-ω-methyl-glutamyl-II (X), respectively; and trans-2-dodecenoic acid replaced by an equimolar amount of 2,4-dodecadienoic acid. Compounds VIII, IX, X are prepared by repeating the procedure of Preparation 4 with N-BOC-L-Thr replaced by an equimolar amount of N-BOC-L-α-amino-n-butyric acid, N-BOC-L-ω-benzyloxycarbonyl-lysine, or N-BOC-L-ω-methyl-glutamic acid, respectively.

What is claimed is:

1. A compound of the formula

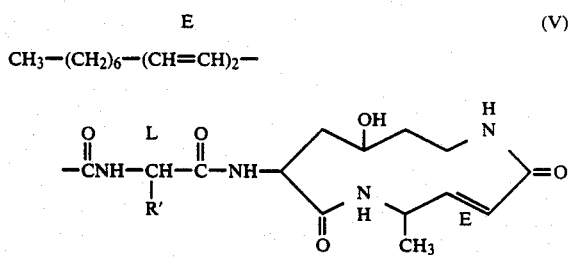

wherein R' is selected from the group consisting of ethyl,

2. A compound according to claim 1 wherein R' is ethyl.

3. A compound according to claim 1 wherein R' is

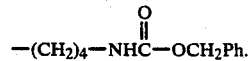

4. A compound according to claim 1 wherein R' is —(CH$_2$)$_2$CO$_2$CH$_3$.

* * * * *